United States Patent
Fischer

[11] Patent Number: 5,969,238
[45] Date of Patent: Oct. 19, 1999

[54] THERMOELECTRIC MICROPROBE

[75] Inventor: Robert Fischer, Ammerbuch-Pfaeffingen, Germany

[73] Assignee: Max-Planck-Gesellschaft Zur foerderung der Wissenschaften E.V., Munich, Germany

[21] Appl. No.: 08/921,179

[22] Filed: Aug. 29, 1997

[30] Foreign Application Priority Data

Aug. 30, 1996 [DE] Germany .......................... 196 35 264

[51] Int. Cl.[6] .......................... G01K 13/00; G01N 25/00; H01L 35/02
[52] U.S. Cl. .......................... 73/105; 136/228; 374/142; 374/120
[58] Field of Search .............................. 73/105; 250/306; 136/228; 374/120, 124, 141, 142

[56] References Cited

U.S. PATENT DOCUMENTS

| | | | |
|---|---|---|---|
| 2,952,725 | 9/1960 | Evans et al. | 136/228 |
| 4,747,698 | 5/1988 | Wickramasinghe et al. | 374/124 X |
| 4,941,753 | 7/1990 | Wickramasinghe | 374/120 |
| 5,356,218 | 10/1994 | Hopson et al. | 73/105 X |
| 5,388,323 | 2/1995 | Hopson et al. | 374/142 X |
| 5,581,083 | 12/1996 | Majumdar et al. | 73/105 X |

FOREIGN PATENT DOCUMENTS

| | | |
|---|---|---|
| 188931 | 3/1957 | Austria . |
| 570239 | 11/1993 | European Pat. Off. . |
| 2458621 | 6/1975 | Germany . |
| 2733071 | 2/1979 | Germany . |

OTHER PUBLICATIONS

M. Stahelin et al., "Temperature profile of fiber tips used in scanning near–field optical microscopy", Appl. Phys. Lett. 68(19), pp. 2603–2605 (May, 1996).

A. Majumdar et al., "Thermal imaging by atomic force microscopy using thermocouple cantilever probes", Rev. Sci. Instrum. 66(6), pp. 3584–3592 (Jun., 1995).

O. Nakabeppu et al., "Scanning thermal imaging microscopy using composite cantilever probes", Appl. Phys. Lett. 66(6), pp. 694–696 (Feb., 1995).

C.C. Williams et al., "Scanning thermal profiler", Appl. Phys. Lett. 49(23), pp. 1587–1589 (Dec., 1986).

*Primary Examiner*—Daniel S. Larkin
*Attorney, Agent, or Firm*—William H. Murray; N. Stephen Kinsella

[57] ABSTRACT

A microprobe for thermoelectric microscopic measurements comprises a probe body (11), which consists of a doped or intrinsically conductive semiconductor material and has at least one thermoelectric contact surface (19). The probe body (11) can carry a metal or semiconductor layer (17), which is separated from the probe body (11) by an insulating layer (16) except in the area of the thermoelectric contact surface (19). A process for the production of a microprobe for thermoelectric microscopic measurements is also given.

8 Claims, 7 Drawing Sheets

THERMOELECTRIC MICROPROBE

The present invention pertains to a microprobe for high-resolution temperature measurement, especially for thermoelectric microscopy, to a process for the production of the microprobe, and to thermoelectric measurement systems using the microprobe.

High-resolution temperature measurements, i.e., temperature measurements of high resolution with respect to position and/or time, are of interest both for characterizing individual points on the surface of a sample and also for the raster scanning of surface areas (thermoelectric microscopy). It is known that microprobes with a geometric shape known from the types of raster scanning microscopy described below can be used for high-resolution temperature measurements.

Figure 5:
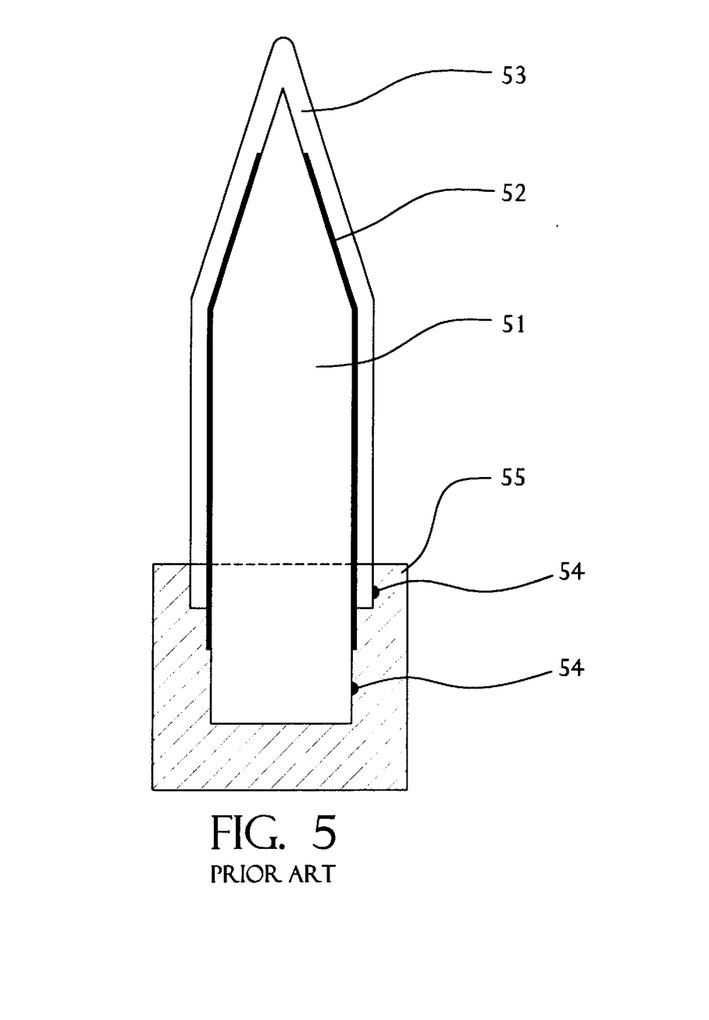
FIG. 5 shows a schematic cross section of a conventional microthermocouple (state of the art)

In the conventional scanning tunneling microscope, needle-like metal tips are used, because these have good electrical conductivity and can be etched to provide them with a tip with a very small radius of curvature. For the simultaneous detection of the topography and temperature profile of a test surface, the use of metal thermoelectric tips is known (C. C. Williams et al.: *Appl. Phys. Lett.*, Vol. 49, p. 1,587, 1986; see also FIG. 5). These modified scanning tunneling probes are designed with a metal probe body 51, which carries a layer of insulation 52, on which in turn a metal layer 53 is deposited. The insulation leaves the extreme tip of probe body 51 exposed, so that a contact surface between probe body 51 and metal layer 53 forms a thermoelectric contact. By providing appropriate contacts for leads 54 (e.g., made of Cu) in the area of a holder 55, a microthermocouple is formed, the tip of which can have a radius of curvature of, for example, about 100 nm.

Microthermocouples of this type suffer from the following disadvantages with respect to their thermal and mechanical properties. The temperature resolution and sensitivity are low, because the thermoelectromotive force of metal thermoelectric tips is limited (e.g., to approximately 0.04 mV/K in the case of the constantan-Au combination). In addition, especially when platinum is used, the mechanical stability of the tunneling tips is low. As a result, deformations or even undesirable lateral oscillations of the tip (limitation of the scanning frequency) can occur during the scanning of a surface when the tip unintentionally makes contact with the sample, which is obviously undesirable but which can occur on occasion. Another disadvantage is that, so far, synthetic resins or micropipette structures have been used as insulation 52 (see FIG. 5), which lead to a considerable increase in the thickness of the probe (loss of positional resolution-). In addition, there is the danger that air bubbles or electrically conductive bridges can form. This increased thickness leads to a decrease in the adhesion of outer metal layer 53. Finally, it is both expensive and complicated to produce these metal microthermocouples.

Figure 6:
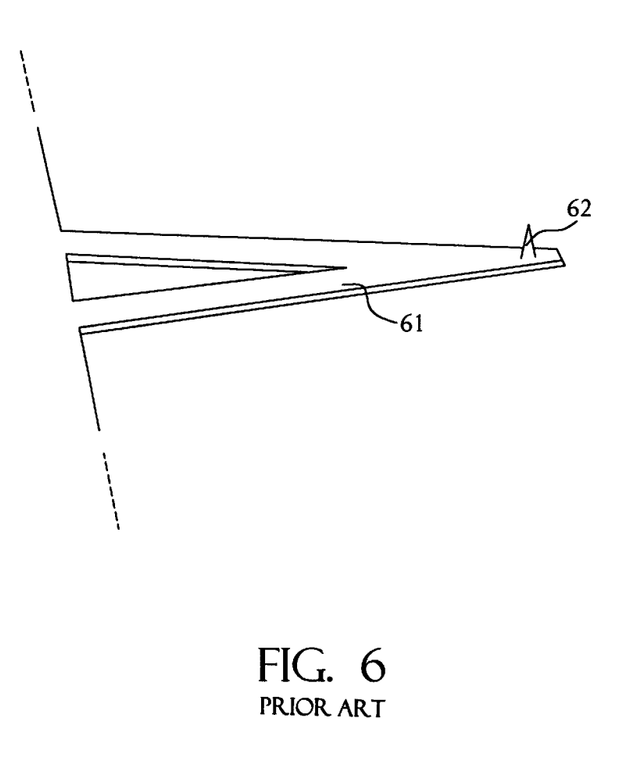
FIG. 6 shows a schematic diagram of a cantilever microprobe.

Probes with a cantilever design are known from atomic force microscopy. A cantilever (see FIG. 6) usually consists of at least one flexible probe body 61 and a pointed area 62 (e.g., in the shape of a pyramid), provided on the side of the probe body facing the surface of the sample. In surface scanning by force microscopy, the probe does not have to be electrically conductive. Therefore, cantilever probe bodies are usually made of semiconductor material, which is more flexible than metal at the relevant dimensions. Cantilever probe bodies are usually made of $Si_3N_4$ or Si.

A modified cantilever design is described by O. Nakabeppu et al. (*Appl. Phys. Lett.*, Vol. 66, p, 694, 1995). For simultaneous atomic force and thermoelectric microscopy, standard $Si_3N_4$ cantilevers were specially provided with a gold or aluminum coating to form microscopic bimetal elements. This known bimetal thermoelectric microscopy suffers from disadvantages with respect to sensitivity, dynamic behavior, and positional resolution.

Cantilever probes which are used simultaneously as both force probes and thermocouples are described by A. Majumadar et al. (*Rev. Sci. Instrum.*, Vol. 66, p. 3,584, 1995). The arms of the probe base body are coated with different metals, which form a thermoelectric contact area in the area of the tip of the probe. These probes are disadvantageous because of the complexity of the processes required to produce them. As an alternative, a cantilever design consisting of two wires is described, which form a thermoelectric contact surface at their contact point. These probes are characterized by the disadvantages of poor stability and poor reproducibility. Finally, probes for thermoelectric microscopy are described, which have diamond tips on atomic-force cantilever probes.

All of the probe designs realized so far for thermoelectric microscopy contain metal-metal thermocouples.

The use of metal microthermocouples is also known from optical near-field microscopy (see, for example, M. St ähelin et al., *Appl. Phys. Lett.*, Vol. 68, The task of the present invention is to provide an improved microprobe and a process for producing it, the new microprobe being characterized by high sensitivity, improved dynamic behavior, and increased stability. The microprobe according to the invention is also to be produced easily anal reproducibly by the use of conventional procedures. Another task of the invention is to provide measurement systems which make use of the microprobes according to the invention.

The task of the invention is accomplished in particular in that, in the case of a microprobe with a probe body shape known from raster scanning microscopy, the probe body consists of doped semiconductor material or a semiconductor material with intrinsic conductivity and has at least one thermoelectric contact surface in the tip area. A thermoelectric contact surface is a section of material which forms a thermocouple when in permanent or temporary mechanical and/or electrical contact with another material. The electrical contact can come about via either the contact resistance or the tunneling resistance. The doping can assume the form of either n-doping or p-doping. Because of the greater mobility of electrons as charge carriers, however, n-doping is preferred.

The doping value is selected as a function of the application and the design in relation to the desired conductivity and thermoelectromotive force of the probe, as discussed further below. On the basis of the relationships between doping concentration, and conductivity (or specific resistance) known from the textbooks (see, for example, "Landolt-Börnstein", New Series, Vol. III/17a, p. 525), it is possible to determine the doping indirectly by way of a resistance value. The total resistance of a probe should be less than 1,000 ohms, which, for the geometry of the tunneling tip, corresponds to a specific electrical resistance of $\delta \leq 1$ Ω-cm. This latter value depends on the application, i.e., on the size of the contact volume. Thus, in the case of minimal contact volume, it may be necessary for the specific electrical resistance to be much smaller than the stated value in order to achieve a total resistance of less than 1,000 ohms. The lower limit of the desired total resistance (maximum doping concentration) is also application-dependent (minimum required thermoelectromotive force). The lower limit of the total resistance can be 1 ohm (or even less in certain special applications), which corresponds to a minimum specific electrical resistance of about 0.1 mΩ.

Instead of a doped semiconductor, a semiconductor with such a small band gap that intrinsic conductivity occurs at the operating temperature can also be used. Examples are Group III-V semiconductors, especially indium antimonite, indium arsenide, and gallium phosphite. The operating temperature (or measurement temperature) refers here to the temperature range in which the probe according to the invention is to be used for thermoelectric microscopy and can comprise in particular the range from low temperatures (a few K) to room temperature or above or to smaller temperature intervals.

The upper limit of the total resistance can also be above 1,000 ohms, if, in a concrete system, a sufficiently small (slow) scanning rate and electrical shielding are made available or if work is carried out with impedance transformers.

Depending on the design and application of the microprobes according to the invention, a distinction can be made between two different embodiments. In a first embodiment, a microprobe or thermoelectric detector is designed as an independent sensor, in which the thermoelectric contact surface in the tip area of the probe body is provided with a metal or semiconductor coating, which forms the thermocouple in cooperation with the thermoelectric contact surface of the probe body. In this case, the probe body is electrically insulated front the coating except in the area of the thermoelectric contact surface. To detect the thermoelectric voltage, the probe body (e.g., the base) and the metal or semiconductor coating are each provided with an electric lead. In a second embodiment, the microprobe or thermoelectric detector is designed as a so-called "unipolar" sensor, in that the thermoelectric contact surface in the tip area of the probe body forms the thermocouple together with the sample material. For this purpose, electrical contact between the thermoelectric contact surface of the probe body and the sample can be established by mechanical contact or by way of the tunneling resistance. The second embodiment as a unipolar sensor requires only one electric lead to the base, for example, of the probe body, over which thermoelectric voltage with respect to the sample is detected.

It is therefore possible to operate both embodiments either with or without mechanical contact. In the case of the first embodiment, this is possible without the need for any further measures, because the sensor operates independently. Depending on the material of the probe body, it may be necessary in the case of the second embodiment to take measures to prevent the formation of an oxide layer on the body. This can be done in particular by alloying a metal layer into the thermoelectric contact surface. This alloy layer has the sole job of preventing the formation of oxide. The microprobe according to the first embodiment forms a closed, thermoelectric measurement circuit. In the second embodiment, all open thermoelectric measurement circuit is formed, which is closed by the sample or sample surface. For this purpose, the sample (or sample surface) must be electrically conductive at least in the range in which the temperature measurement occurs. In addition, the sample must be electrically contacted, which can be done by means of a connecting wire, a second metal probe tip, or a special design of the sample holder. It is possible, for example, to ground the sample holder and thus the sample along with it, and to take the measurement of the thermoelectric voltage between the probe body of semiconductor material and ground. This is advantageous because of the short response times of microprobes according to the invention especially in measurements at high frequencies.

If the probe is provided with an electrically conductive coating, it if preferable for this coating to consist of a metal layer (e.g., Ag, Au) with a thickness of $\geq 0.3$ nm.

The microprobe according to the invention can be realized in the form of any design with a terminal area which makes it possible to form at least one probe tip pointing toward the sample. In particular, the tunneling tip form, the cantilever form, or any other suitable needle-like, pyramidal, conical, or tapered form can be used.

For the tunneling tip design, it has been found that the conventional metal probe bodies can be advantageously replaced by a doped semiconductor. As the degree of doping increases) the conductivity of the semiconductor material increases also (the resistance decreases), but the thermoelectromotive force decreases. The doping is therefore selected according to the invention in such a way that the conductivity is sufficient for the measurement of the thermoelectric voltage and/or tunneling currents. According to a special embodiment, the doping is selected so that the resistance of the probe body is less than 1,000 ohms. For special applications requiring especially good dynamic behavior, a resistance on the order of 100 ohms (or less) is preferred.

For the cantilever design, it has been found to be advantageous according to the invention to depart from the known design in which the cantilever is made of semiconductor material and to use instead a doped semiconductor material which itself forms the thermoelectric contact surface in the tip area. The doping of the semiconductor material is again selected so that a sufficiently low resistance (dynamic behavior) or a sufficiently high thermoelectromotive force is achieved. When the cantilever design is used, furthermore, the total resistance of the probe body is again preferably less than 1,000 ohms, especially about 100 ohms.

The thermoelectric probes according to the invention are characterized by high thermoelectromotive force. In addition, they are extremely stable and are resistant to undesirable (especially lateral) oscillations.

It is possible and advantageous to make the monocrystalline or polycrystalline probe body by the use of a method known in and of itself, i.e., by wet-chemical etching or by microstructuring on a semiconductor wafer. To produce a probe body of doped semiconductor material according to the first embodiment mentioned above, all insulating oxide layer (possibly a foreign oxide) is deposited, and then the tip area of the probe is bared to form the thermoelectric contact surface. The thermoelectric contact surface is preferably bared by wet-chemical etching, by ion-beam etching, or by reactive etching, as used in planar technology. The latter type of etching with reactive gases can be conducted in vacuum systems.

SUMMARY

There is provided herein a microprobe for thermoelectric microscopic measurements and method for producing same. According to one embodiment of the invention, the microprobe comprises at least one probe body, which has at least one probe tip and at least one feed electrode, wherein the probe body consists of a monocrystalline or polycrystalline semiconductor material and has at least one thermoelectric contact surface, on which a thermocouple is formed with a metal or semiconductor layer, wherein the semiconductor material is either doped or has such a small band gap that intrinsic conductivity occurs at the operating temperature. According to another embodiment of the invention, the thermoelectric contact surface of the microprobe is exposed at the probe tip or is provided with an alloy layer.

BRIEF DESCRIPTION OF THE DRAWINGS

Embodiments of the microprobe, of the process for its production, and of measurement systems using the microprobe according to the present invention are described below with reference to the drawings.

DETAILED DESCRIPTION OF PREFERRED EMBODIMENT(S)

The embodiments of the invention are described in the following on the basis of the scanning tunnelling design with a silicon probe body. The invention is not limited to this example, however; on the contrary, it can also be realized with other doped semiconductor materials or mixed semiconductors or with other designs (especially the cantilever design).

Figure 1:
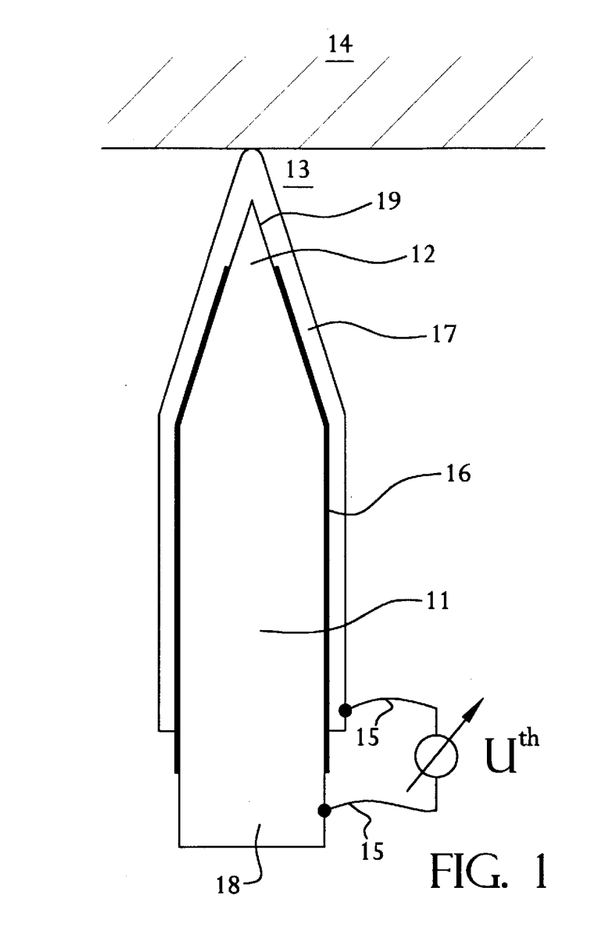
FIG. 1 shows a schematic cross section of a first embodiment of the microprobe according to the invention with the scanning-tunelling tip design.

FIG. 1 shows a schematic cross section of a microprobe according to the invention for use as an independent thermoelectric tip (first embodiment). The microprobe can be used in contact with a sample (shown) or at a predetermined measurement distance from it (order of magnitude application-dependent) for measurement either in air (from about 5 $\mu$m or less, down to the Angström range) or in a vacuum (from about 0.5 $\mu$m or less down to the Angström range). The microprobe comprises a mono- or polycrystalline probe body 11, which consists of a doped semiconductor material. Probe body 11 has a base area 18, to which at least one electrical lead 15 can be attached and which can be mounted in the holding or scanning device of a measuring system, and a tip area 12, which tapers down in a needle-like manner and which is directed toward sample 14 when in the measuring position. Probe body 11 is partially covered by a layer 16 of insulating material. Insulating layer 16 is designed so that tip area 12 and base area 18 of probe body 11 are exposed. Insulated probe body 11 and the exposed part of tip area 19 are covered by a metal layer 17. The uncovered or uninsulated part of tip area 12 forms a thermoelectric contact surface 19, which forms a thermocouple together with the adjacent part of metal layer 17. The thermoelectric voltage U$_{th}$ occurring at the thermocouple can be tapped via leads 15. It is also possible for protective or insulating layers (not shown) to be provided especially in the base area of the probe.

The dimensions of the illustrated microprobe correspond to those of commonly used scanning tunnelling probes. Thus, probe body 11 can have a diameter of preferably about 0.1–0.3 mm and a length of about 2–10 mm, preferably about 5 mm. Diameters as small as 0.05 mm or as large as 0.5 mm or more, however, are also possible. Depending on the geometric relationships (length, thickness), the angle formed by the tip of the probe is about 10°. The thicknesses of insulation layer 16 and of metal layer 17 are optimized in such a way that sufficient insulation is provided and so that a stable covering of the thermoelectric contact surface 19 of tip area 12 is ensured. At the same time, these layers should not be made any thicker than necessary; otherwise, the probe will become too thick, and the positional resolution will suffer. The layers are preferably at least 100 nm thick.

Probe tip 13 thus consists of metal layer 17 on tip area 12 with the contact surface. Probe tip 13 forms the temperature-sensitive volume, the features of which are determined in particular by the curvature of the probe tip (radius of curvature, e.g., 1 $\mu$m to 0.2 nm) and by the size of contact surface 19 (characteristic distance between the edge of insulating layer 16 and the end of the tip, e.g., 20 $\mu$m or less, down to the radius of curvature of the tip).

The degree of doping of the semiconductor material of probe body 11 is selected as a function of the type of application and the surrounding conditions. The semiconductor must be doped highly enough to ensure that electricity will be conducted. The doping should not be too high, however, because, as the doping concentration increases, the thermoelectromotive force decreases. The desired degree of doping can be optimized on the basis of the known properties of doped semiconductors. In determining the total amount of tip resistance which can be allowed, it should be remembered that a high resistance (>1,000 ohms) is associated with interfering Johnson noise (and possibly, if the shielding is insufficient, the capture of high-frequency interference, which represents all increasing proportion of the signal as the resistance increases) and that, especially for dynamic measurements, the time constant (RC time of the measurement circuit) should be low (e.g., $\leq 1$ $\mu$s for short signal times).

For rapid temperature measurements (ns range), doping with arsenic, for example, has been found advantageous for the formation of n-Si with a doping concentration of $2.5 \cdot 10^{19}$ 1/cm$^3$. A microprobe doped in this way has a thermoelectromotive of about 0.8 mV/K (at 300 K). The invention is not limited, however, to the indicated doping material or its concentration. Instead, any other materials and concentrations can be used which best fulfill the above-cited optimization as a function of the application in question.

The probe body can be formed by a semiconductor material with intrinsic conductivity. For this purpose, Group III-V semiconductors are especially suitable, e.g., indium antimonite, indium arsenide, and gallium phosphite. Indium antimonite has a specific resistance of about 5 m$\Omega$-cm and a relatively high thermoelectromotive force of about 300 $\mu$V/K at room temperature, which increases even more as the temperature decreases to 200 K. Indium arsenide has a similarly high thermoelectromotive, but a higher specific electrical resistance of 300 m$\Omega$-cm. All intrinsic semiconductors offer the advantage that it is easy to create a thermoelectric contact surface in contact with a metal, because, as a result of the small band gap, no Schottky barrier at all or one which offers no interference is formed.

Metal layer 17 consists of a material which conducts electricity such as gold, platinum, or copper.

The microprobe shown in FIG. 1 can be modified as follows:

First, it is possible to provide the uncovered areas of probe body 11 (base area 18 or tip area 12) at least partially with an alloy to prevent the formation of a Schottky barrier. In particular, it is possible to replace metal layer 17 with an alloy layer. In such an embodiment, layer 17 represents an alloy layer 17. The way in which the alloy is provided will be described in detail further below in conjunction with a description of the process according to the invention. It is not absolutely necessary to provide an alloy layer. For example, it has been found that highly doped germanium tips, which can be operated in contact with a copper sample, result in a sufficiently low-ohmic measurement circuit. In general, the alloys can be omitted when highly doped semiconductors are used. "Highly doped" means here that the semiconductors show "degenerate" behavior. This mean that the doping is so strong that the Fermi energy is within the effective conduction band formed by the fusing of the conduction band of the semiconductor with the extrinsic band. Materials with a behavior of this kind offer the advantages that the resistance at low temperatures is not only low but also nearly constant and that it increases with rising temperatures (the behavior therefore being similar to that of metals).

Second, it is also possible to replace metal layer 17 with a semiconductor layer. To ensure optimum conductivity or thermoelectromotive force, the semiconductor layer is doped in a suitable manner, or a suitable intrinsically conductive semiconductor element is used. So that lead 15 can be attached to the semiconductor layer, it can be necessary again to provide an alloy layer on this semiconductor to prevent the formation of a Schottky barrier. Conversely, it is also possible in accordance with the invention to apply a suitably doped semiconductor layer or a layer of a semiconductor with intrinsic conductivity to a metal probe body. The sputtered-on or vapor-deposited semiconductor, however, is amorphous and may possibly require passivation with hydrogen (to saturate the "dangling bonds"). A transformation of the amorphous into a crystalline structure can be realized by known methods involving the input of energy (irradiation or heating). In regard to this design, everything said above about geometry and material selection in the case of a probe with a semiconductor body applies in an analogous manner.

Third, it is possible to omit both insulation layer 16 and metal or semiconductor layer 17 when the microprobe is operated in contact mode and the sample forms a part of the thermocouple in the measurement circuit or when the microprobe is used under vacuum at such a short distance from the sample surface that the contact resistance to the sample (corresponding to the tunneling resistance) is minimized (e.g., no more than about 50 k$\Omega$). This modification is described further below in reference to FIG. 2.

In the following, a process for producing a microprobe according to the invention is described on the basis of an example of the scanning tunnelling tip design. The processing steps and materials can be modified as a function of the selected material and design.

The first step of the process is to prepare the probe body. First, the doped or intrinsically conductive monocrystalline or polycrystalline semiconductor material is shaped into a pin-like body, which has essentially the same proportions as those of the desired probe body. This shaping is done, for example, by mechanical processing of the material. Then the semiconductor blank is reduced to the desired size of the probe body by wet-chemical etching. Wet-chemical etching (e.g., with the use of hydrofluoric acid, HF) offers the advantage of being a method commonly used in the fabrication of planar semiconductor chips and is thus readily available. As a substitute or in addition, it is also possible, however, to etch the blank by electrochemical means. This can be advantageous especially in regard to the shaping of the tip area. In addition, (exclusively or in a supplemental processing step), anisotropic etching can be used to form the tip. This is preferred in particular for the cantilever designs.

The semiconductor blank can have either a round or a polygonal cross section. The concentration of the etching bath is suitably selected so that the etching proceeds neither too quickly (so that the dimensions of the probe body can be controlled) nor too slowly (e.g., to avoid undesirable anisotropic etching). Thus, in a so-called HF dip for exposing oxidized semiconductor regions (e.g., $SiO_2$), an $HF:H_2O$ ratio of about 1:4 can be used. After an etching time of about 30 seconds, the HF is removed in a water bath, and the etched surface is dried. For etching shapes, an $HF:NHO_3$ mixture can be used, in which case a larger amount of $HNO_3$ produces smoother structures, whereas a larger amount of HF (or $H_2O$) produces rough structures. Preferably 40 vol. % of HF and 70 vol. % of $HNO_3$ are mixed in a ratio of 1:3. Finally, a mixture of HF (concentrated):$HNO_3$:acetic acid in a ratio 3:5:3 can be used. Etching is carried out preferably at room temperature.

In the next step of the process, a layer of oxide is applied to the etched probe body to provide the insulating layer. The oxide layer can consist of the natural oxide of the semiconductor body or of a foreign oxide.

To provide a probe body of doped silicon with effective insulation, the silicon is thermally oxidized, so that initially a closed oxide layer covers the entire probe body. Oxidation is carried out preferably at about 1,000° C. in such a way that a layer about 100 nm thickness is obtained. Thermal oxidation of the Si probe body offers the advantage that the $SiO_2$ forms a reliable and extremely thin insulating layer, which is also very hard and resistant to mechanical and chemical influences.

A layer of $SiO_2$ can also be applied, e.g., by deposition front the vapor phase, to other semiconductor materials (e.g., germanium). As an alternative, it is also possible to use synthetic resins or any other suitable insulating materials (e.g., lacquers, especially photosensitive resists; ceramics; glass; Plexiglas; or the oxides, nitrides, and fluorides such as $Al_2O_3$, AlN, $Si_3N_4$, or $CaF_2$ known from semiconductor technology) as the insulating layer.

In the next step of the process, the base and tip areas of the insulated probe body are bared to create a contact surface for the electrical lead and to form the thermoelectric contact, respectively. The locally selective removal of the oxide or synthetic resin layer can be done by photolithography, for example. For this purpose, the insulated probe body is coated with a layer of a photoconductor and illuminated in a suitable manner. After the photoconductor above the areas to be exposed has been removed, these areas are etched by the wet-chemical method to expose the base and tip areas. As an alternative which is especially suitable for very small sensitive volumes, it is also possible to use ion beam etching.

To avoid the formation of Schottky contacts, it may be necessary, in an additional step of the process, to provide the exposed semiconductor surface with an ohmic contact layer with a thickness of about 200 nm. Depending on the type of semiconductor and the type of doping, a suitable metal (or combination of metals) is deposited from the vapor phase or sputtered on and then alloyed-in at about 400–600° C. for about 10 minutes. The alloying material is selected so that a low-resistance electrical contact with the semiconductor material is obtained. Thus, for example, p-doped germanium or silicon can be provided with an alloy of gold (with 1% aluminum) or of aluminum, and n-doped germanium or silicon can be provided with an alloy of gold (with 1% antimony). The alloying is carried out in an argon atmosphere at about 600° C. for silicon and at about 475° C. for germanium. For the ohmic contacting of GaAs (in the case of n-doping), 200 nm of Au (12% Ge) and then 40 nm of Ni are applied in succession and then alloyed-in at about 450° C. for about 80 seconds under a forming gas (e.g., $H_2$ in Ar).

The alloy layer can be applied to the base and tip areas either simultaneously or in succession. The alloy areas offer the advantage of high mechanical stability. In the case of open systems (compare FIG. 2, see below), contact with the sample does not lead directly to abrasion at the tip of the probe.

Finally, the outer metal layer is deposited (e.g., from the vapor phase or sputtered on). The material of this outer metal layer is selected from the standpoint of good conductivity and good adhesion. Gold is the preferred material. Instead, it is also possible, however, to apply first a layer of Cr and then a layer of Au, where the Cr serves as a bonding agent to the $SO_2$ (formation of chromium oxide). In this case, the ratio of the layer thicknesses will be approximately in the range of Cr:Au=1:10. The outer metal layer can thus also consist of multiple layers.

The last step of the process is to attach the leads in a suitable maimer to the base area of the probe body and to the outer metal layer. This is done, for example, by clamping them on or by cementing them on with an electrically conductive adhesive (e.g., a silver epoxide adhesive). The leads are attached preferably at point of equal temperature, e.g., inside a holder, which serves as a heat bath.

Alternative methods for forming the insulation layer can be realized as follows. First, it is possible to dip the tip to be insulated, possibly several times, into an HF-resistant lacquer (e.g., a photosensitive resist) and to turn the tip over in such a way that the lacquer runs down from the tip area to the probe body until a minimum tip area is exposed and the probe body is insulated. It is also possible to apply a protective layer, as insulation, to the probe body with a microbrush under the microscope.

The process described is modified in the production of cantilever designs in the sense that the cantilevers are produced in the conventional manner on semiconductor wafers and then subjected to the following steps of providing insulation, selectively exposing certain areas, and forming contacts as described above. Here, too, an alloying step can be provided. These steps can be integrated in an advantageous manner into known semiconductor production processes. Preferably monocrystalline Si wafer material is used in conjunction with anisotropic etching methods.

In accordance with an alternative procedure for forming thermoelectric tips with especially high positional resolution and/or especially good dynamic behavior, it is proposed that the tip of the probe be formed not by processing (reducing the size) of a blank but rather by a growth process. Thus, probe tips of the smallest possible dimensions (e.g., with a length of about 10 $\mu$m) similar to "whisker" crystals) can be grown. It is also possible to combine the two approaches, namely, the processing of blanks and the growing of crystallites, with each other, e.g., by growing a needle-shaped crystallite on a probe tip produced by the method described above.

Figure 2:
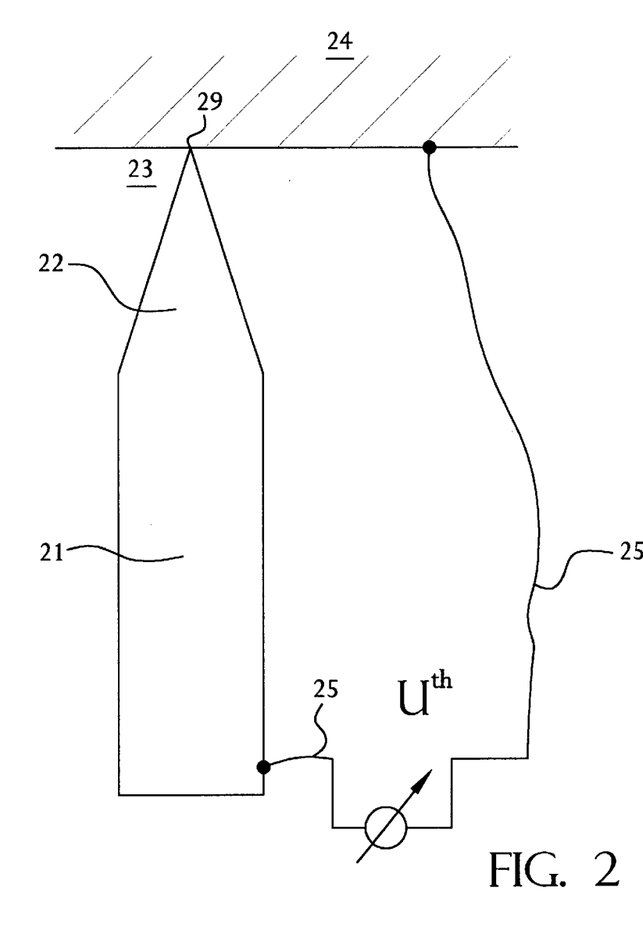
FIG. 2 shows a schematic cross section of a another embodiment of the microprobe according to the invention.

FIG. 2 shows the second embodiment of the invention, for cases in which measuring is done in contact with an electrically conducting sample or an electrically conductive sample surface (e.g., an insulating sample with a thin, electrically conductive coating). In contrast to the first embodiment according to FIG. 1, the thermocouple is formed here by setting probe tip 23 of tip area 22 down onto sample 24 or by bringing probe tip 23 close enough to sample 24 to allow the passage of electric tunneling current. As a result, the sensitive volume in the tip-sample contact area 29 is minimized. The thermoelectric voltage $U^{th}$ can be tapped via leads 25 attached to probe body 21 and to the sample surface.

The design of probe body 21 is simpler than that of the first embodiment, because no additional coatings are required beyond an ohmic alloy layer to form an electric contact at the base of the probe body and possibly an additional ohmic alloy layer at the tip of the probe body (see the details below), the probe body itself thus being completely bare.

The second embodiment can be realized with doped germanium. Germanium forms a relatively soft oxide layer, which can be easily penetrated by contact with the sample. In principle, however, any semiconductor which has either no insulating surface layer at all or, like Ge, only a weakly adhering one (e.g., an oxide layer) is suitable.

But it is also possible to produce the probe body out of a semiconductor material with a strongly adhering or hard oxide layer (e.g., Si) for contactless measurements corresponding to the second embodiment. In this case, tip area 22 (apex of the semiconductor tip) is provided with an alloy layer. This alloy layer consists of a metal which is suitable for ohmic contacting but is not provided with an electric lead; on the contrary, it serves merely to form an electrical bridge with respect to the sample surface while preventing the formation of an oxide layer.

The embodiment according to FIG. 2 offers the advantage of a simplified design (and of a simplified production process), but it must usually be operated under vacuum or under inert gas conditions or with the addition of an alloy layer on apex to avoid the formation of oxide at the tip of the probe when the measurement are being made without mechanical contact between the tip and the sample (raster probe technique) and/or when semiconductor materials with a strongly adhering, insulating surface layer (e.g., Si) are used. Probes of this type are produced at least in part in the same way as described above. This means in particular that, first, a blank is produced and then reduced in size as described above by etching, for example. After the base area of the probe body has etched (e.g., in an HF dip) to expose it by eliminating a natural oxide layer, an ohmic layer is alloyed in at the base of the probe and a lead contact is formed. In addition, it can be provided that the apex is first etched in an HF dip to expose it and then provided with an ohmic alloy layer. The design according to FIG. 2 can be realized in an analogous way to create a cantilever structure.

Preferred applications of the embodiment according to FIG. 2 are to be found in the room-temperature to low-temperature range and in combination with scanning-microscopy sensor systems designed to record surface profiles or topographies. Measurement in the low-temperature range is especially advantageous when the probe body is made out of a degenerate semiconductor material, because this material shows a metal-like behavior in the low-temperature range (room temperature down to a few K) and is therefore highly suitable for the formation of a thermoelectric contact surface.

Measurement systems based on the use of the microprobes according to the invention are described in the following with reference to FIGS. 3 and 4.

Figure 3:
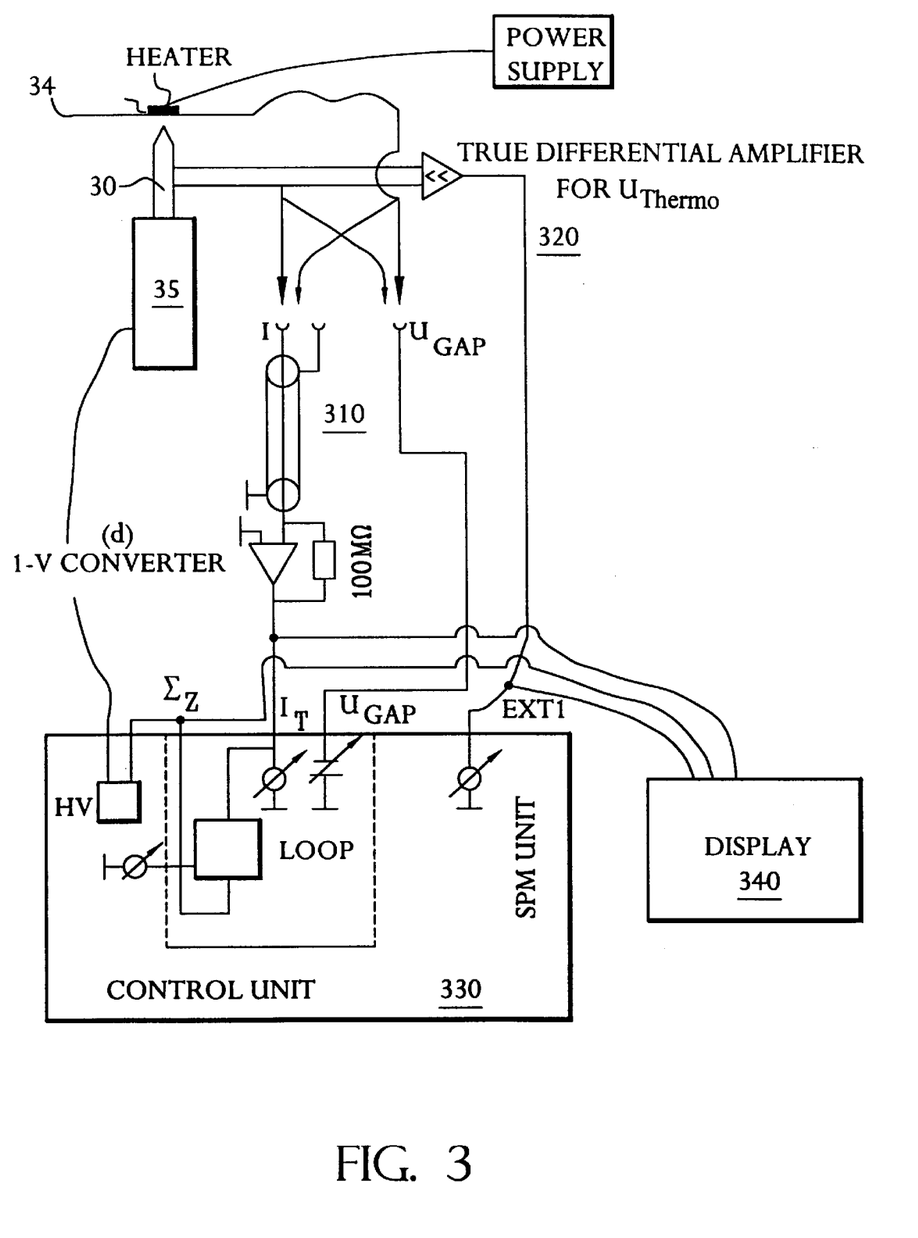
FIG. 3 shows a pictorial schematic of a measurement system for simultaneous scanning tunnelling and thermoelectric microscopy.

FIG. 3 shows the basic circuit diagram of a measurement system, in which the measurement probe according to the invention is used simultaneously for scanning tunnelling and thermoelectric microscopy. Needle 30 can be positioned and manipulated with respect to sample 34 by means of an adjusting device 35 (e.g., a piezoelectric tube); the sample can be heated if desired. Needle 30, which can be designed in accordance with, for example, FIG. 1, makes it possible for tunneling current measurement channel 310 and temperature measurement channel 320 to be operated in a truly parallel manner. The adjusting device and the measurement channels are controlled by a control Unit 330. A display unit 340 (e.g., an oscillograph) is provided for manual tuning of the control operations and for displaying the measurement signals. In FIG. 3, furthermore, the following terms are employed to label the selected illustrated features thereof: heater, power supply, true differential amplifier for $U_{th}$, I→V converter, loop, and SPM unit.

Figure 4:
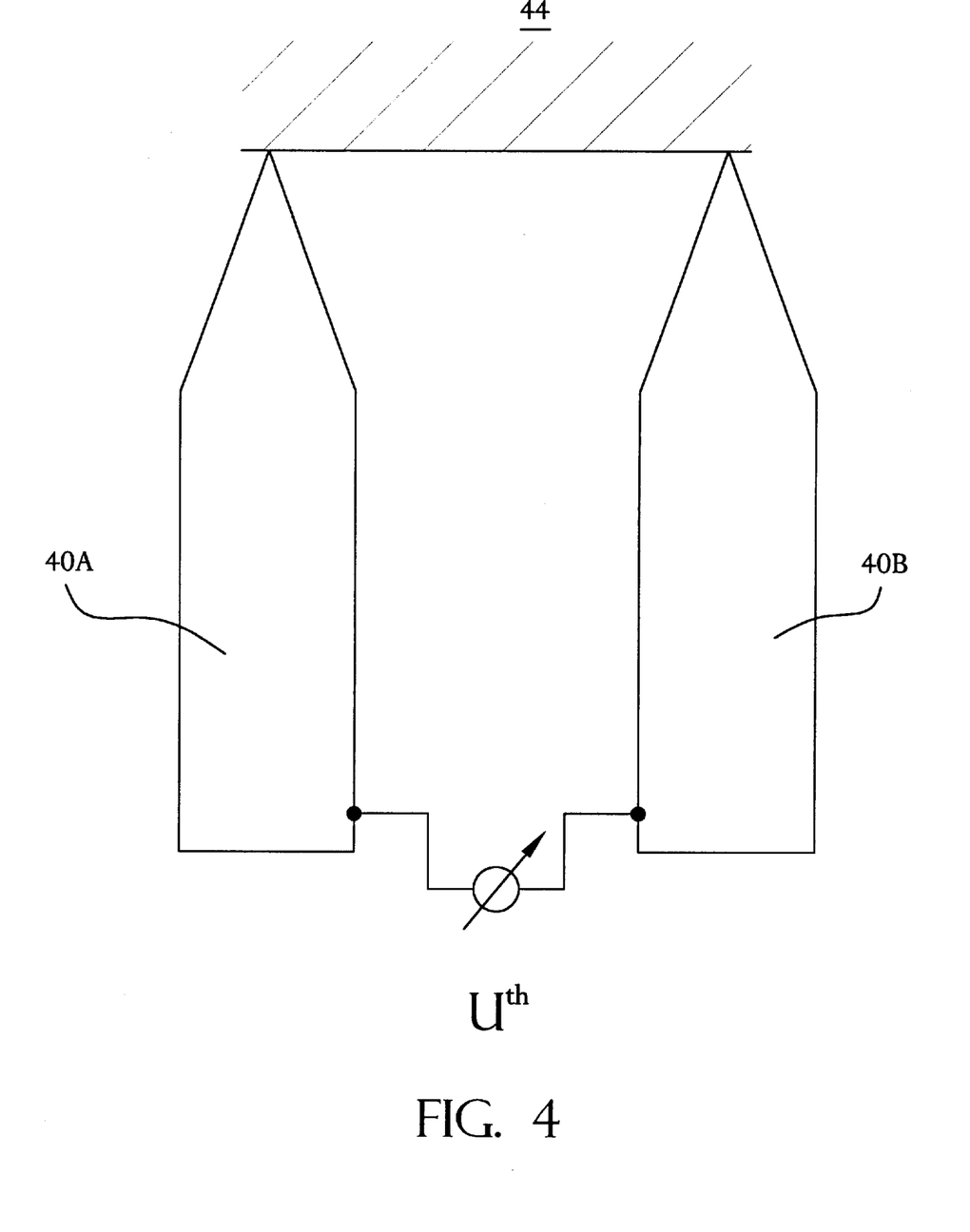
FIG. 4 shows a schematic, diagram of a microprobe measurement system for determining the thermal conductivity of a sample.

FIG. 4 shows the example of a multi-tip system for use either for sample contacting according to FIG. 2 or for determining the thermal conductivity of a sample in analogy to the so-called "rod" method. In the rod method, an essentially one-dimensional body of the material to be studied is connected at one end to a heat source and at the opposite to a beat sink, so that the thermal conductivity can be calculated from the temperature gradient which develops. The microprobes according to the invention allow a simple transfer of this measurement principle to any desired material and material form. This is achieved in that several, preferably identical, microprobes are placed on a sample with temperature gradients to tap the thermoelectric voltages corresponding to the temperature differences. Two microprobes are preferably arranged in a common holder, as known from so-called tip test devices in semiconductor process technology. Microprobes 40A, 40B are preferably built like the microprobes shown in FIG. 1 or FIG. 2. To simplify their calibration, the two microprobes are of identical design. But it is also possible, as an alternative, to use different semiconductors or to combine a semiconductor microprobe according to the invention with a conventional metal microprobe. If sample 44 is electrically conductive or provided with electrically conductive surface coating (e.g., a metal layer), microprobes according to FIG. 2 are placed on it. Otherwise, microprobes according to FIG. 1 are used.

Additional measurement systems pertain to the measurement of additional thermophysical properties (diffusivity, heat capacity, contact resistances) by electrical and optical dc, pulse, ac, or relaxation methods. In addition, it is possible to combine surface scans with temperature measurements in profilometers. Thus, probes according to the invention make it possible, in a simple way, to detect structures in the micrometer range during the scanning of semiconductor chips or to record temperature distributions in conductive pathways. Finally, applications in scanning thermoelectric microscopy are also conceivable, in which a probe tip is heated and its cooling is detected as a function of its location on the sample. Further measurement systems comprising a microprobe according to one of the above embodiments are systems for simultaneous tunnel and thermoelectric microscopy, systems for simultaneous atomic force and thermoelectric microscopy, systems for simultaneous optical near field and thermoelectric microscopy and systems for determining thermophysical properties of a material by time and/or position resolved measurements of temperatures and/or temperature changes.

Microprobes according to the invention can be combined in an advantageous manner for the simultaneous detection of temperature and topography in SNOM measurement systems (SNOM=Scanning Near-Field Optical Microscope). It has been found that the positional resolution of microprobes according to the invention is in the sub-micrometer range and thus is suitable for the recording of topographical images, which can be combined simultaneously with temperature profiles.

The microprobes according to the invention offer the following advantages: Because of the high thermoelectromotive force of semiconductor materials, the microprobes according to the invention are much more sensitive (by about two orders of magnitude) than metal microthermocouples. In addition, they have greater mechanical and chemical stability. The sensitive volume of the probe (contact surface) can be minimized, so that extremely short signal rise times in the ns range cam be achieved. A positional resolution of less than 100 nm can be reached. Temperatures can be measured without contact. Because of their compatibility with probes of conventional microscopy methods, the microprobes according to the invention are suitable for use in a wide variety of applications.

Figure 7:
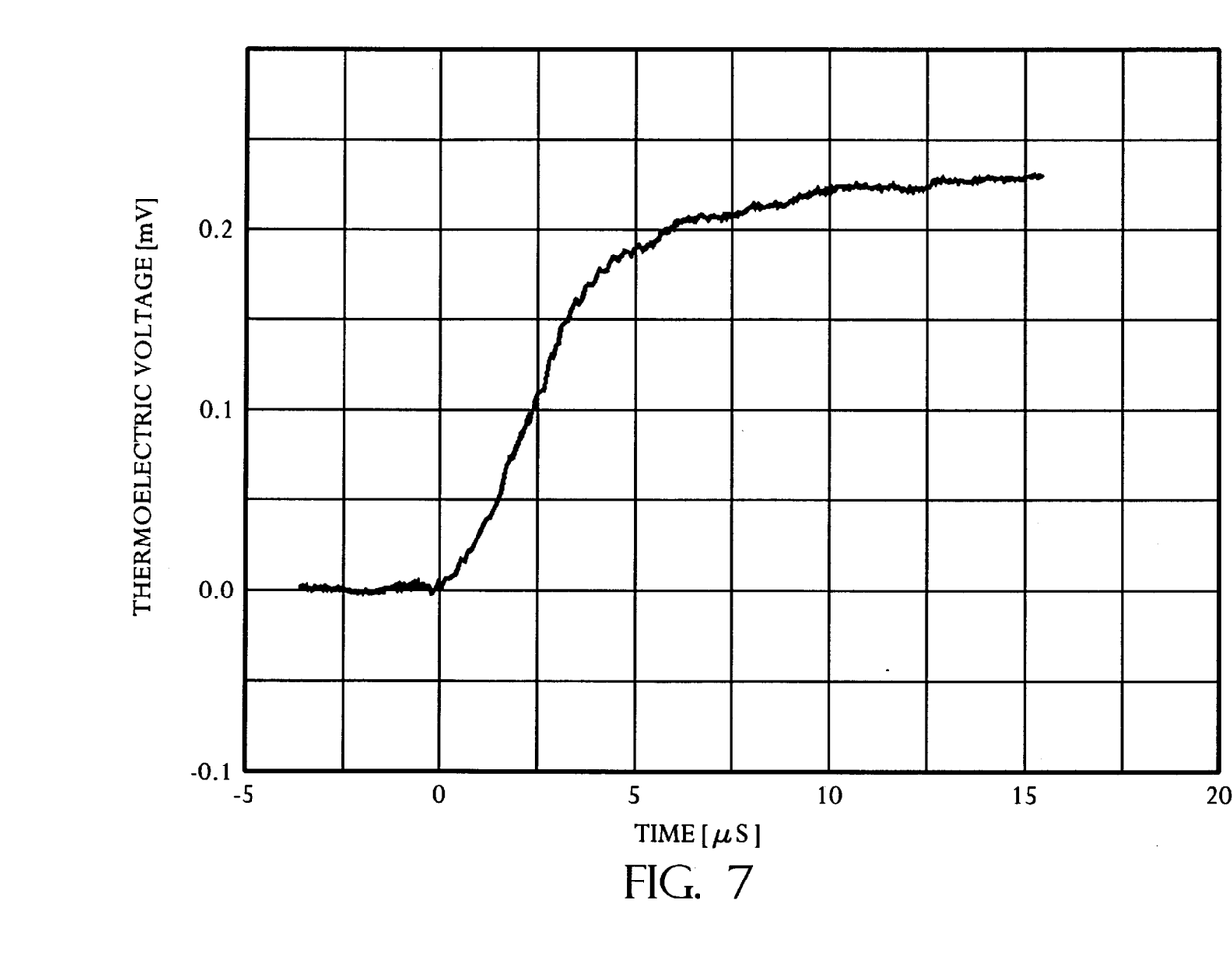
FIG. 7 shows a curve of the response time of a microprobe according to the invention.
Figure 8:
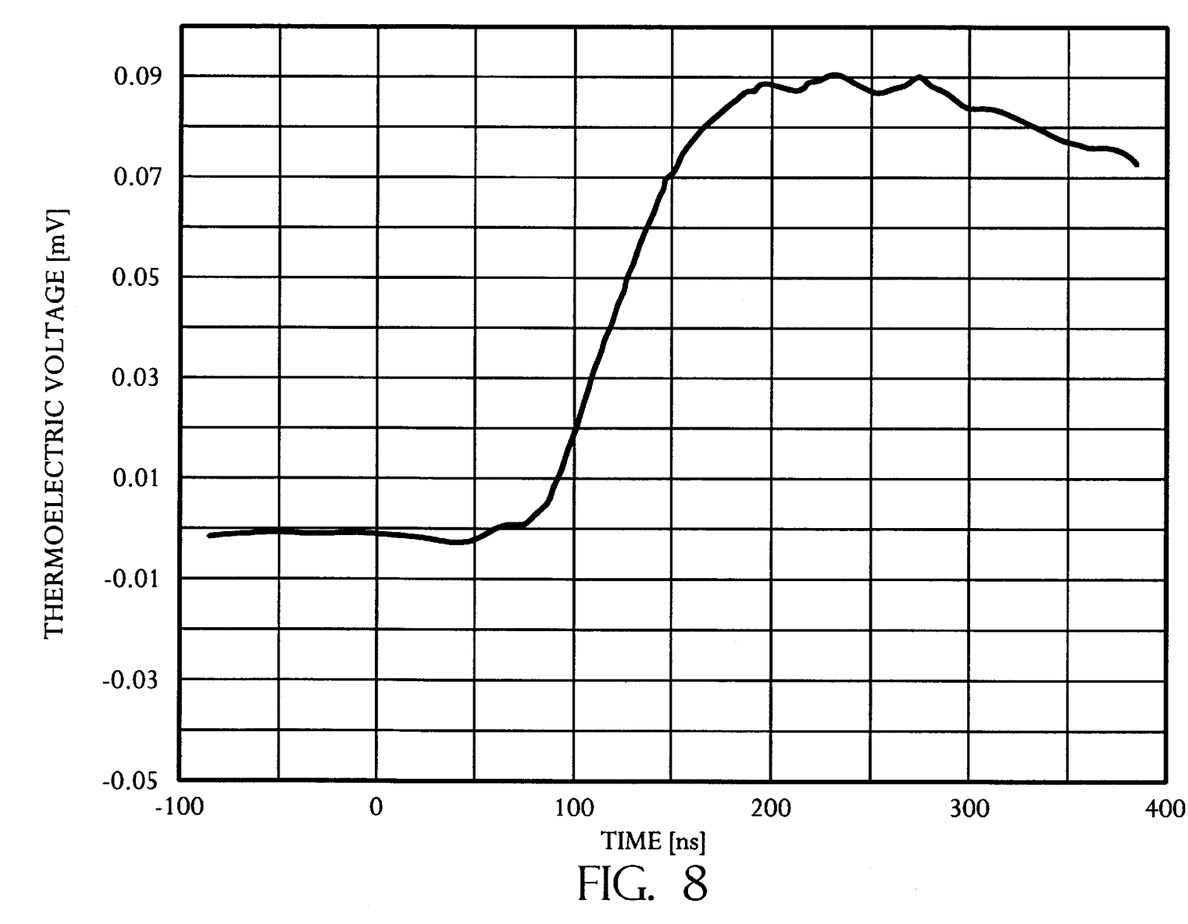
FIG. 8 shows another curve of the response time of a microprobe according to the invention.
Figure 9:
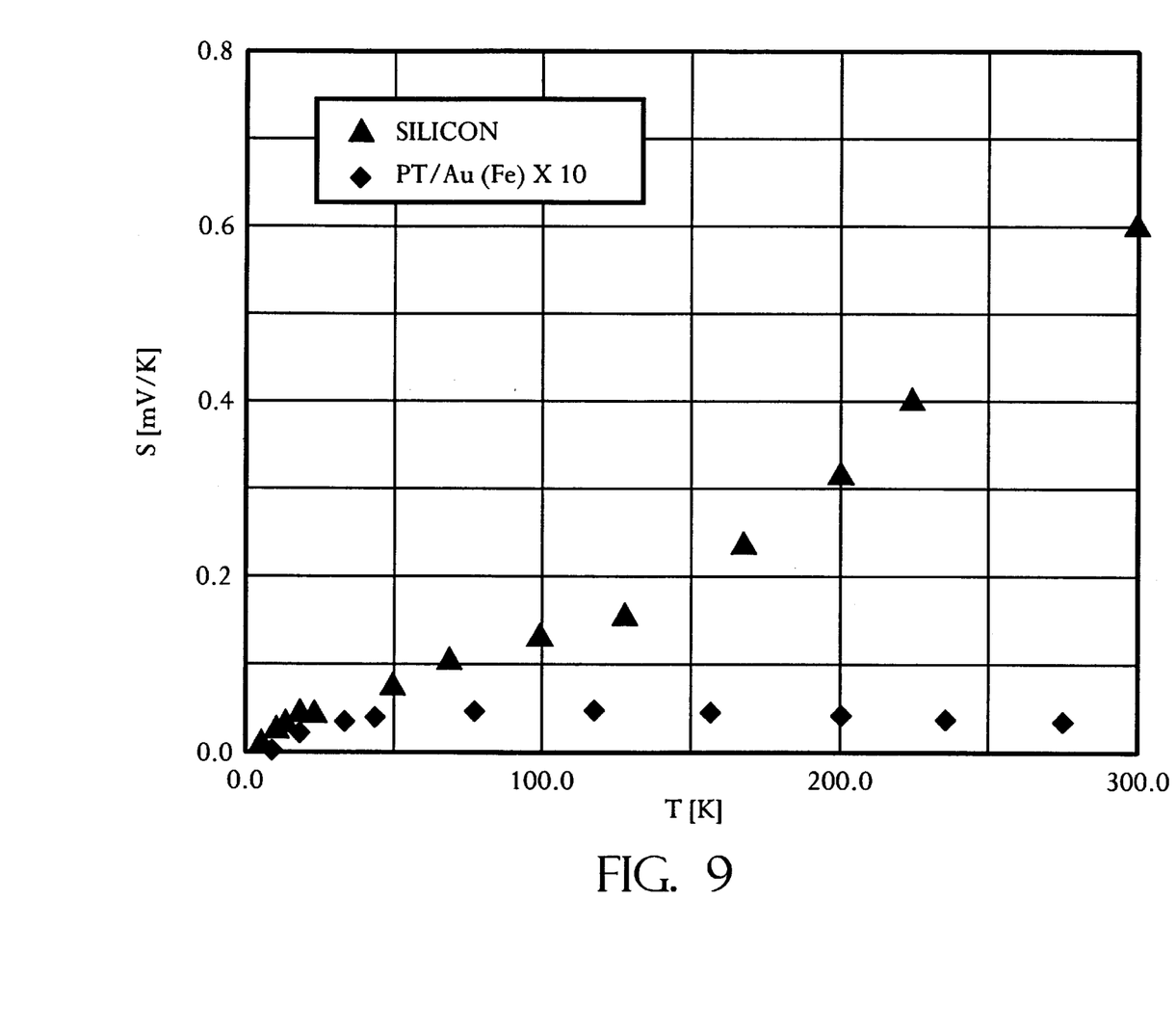
FIG. 9 shows curves of the thermoelectromotive force of a microprobe according to the invention and of a conventional metal thermocouple.

FIGS. 7, 8, and 9 illustrate the indicated advantages by way of example. For the measurement of the signal rise time (or response time) of microprobes according to the invention, the front of a plate-shaped sample was exposed to a heat pulse in a so-called laser-flash measurement, and the time dependence of the temperature was measured on the back. Since the thickness and thermal conductivity of the sample are known, the time dependence makes it possible to determine the response time of the thermoelectric microprobe. FIG. 7 shows a measurement result for the rise of the thermoelectric voltage in the case of a Cu sample (thickness: 45 μm) at T=295 K after exposure to a Nd:YAG laser for 8 ns. The thermoelectric voltage determined from the time dependence of the microprobes according to FIG. 1 or FIG. 2 shows response times in the ns range. The response time in the case of the microprobes according to FIG. 2 is even shorter, as can be seen from the experimental results for corresponding measurements of a sample layer thickness of 400 nm (FIG. 8).

FIG. 9 shows the thermoelectric force of microprobes according to the invention as a function of the operating temperature in comparison with the thermoelectric force of conventional thermocouples of metal. The superior properties of microprobes according to the invention over the entire measurement time range of interest are obvious.

The process according to the invention for the production of the microprobes is advantageous especially because it can be combined with conventional procedures of semiconductor process technology. In addition, the process allows large numbers of microprobes to be produced at low cost and in a reproducible manner. The need to use of semiconductor wires, which are practically unavailable, is avoided.

The measurement systems based on the use of the microprobes according to the invention offer the advantages of greater sensitivity, improved dynamic behavior, and increased reliability.

It will be understood that various changes in the details, materials, and arrangements of the parts which have been described and illustrated above in order to explain the nature of this invention may be made by those skilled in the art without departing from the principle and scope of the invention as recited in the following claims.

What is claimed is:

1. A microprobe for thermoelectric microscopic measurements, comprising at least one probe body, which has at least one probe tip and at least one lead electrode, wherein the probe body consists of a monocrystalline or polycrystalline semiconductor material and has at least one thermoelectric contact surface, on which a thermocouple is formed with a metal or semiconductor layer, wherein the semiconductor material is either doped or has such a small band gap that intrinsic conductivity occurs at the operating temperature, wherein the probe body carries, in sequence, an insulating layer and the metal or semiconductor layer in such a way that the thermoelectric contact surface of the probe body is formed by a part of the tip area of the probe body not covered by the insulation layer, and so that the metal or semiconductor layer is electrically insulated from the probe body except in the area of the thermoelectric contact surface.

2. The microprobe of claim 1, wherein the semiconductor material is doped in such a way that the resistance of the probe body at room temperature is less than 1,000 ohms.

3. The microprobe of claim 1, wherein the semiconductor material is silicon, germanium, gallium arsenide, III-V semiconductors, or mixed forms of these materials.

4. The microprobe of claim 1, wherein the thermoelectric contact surface is provided with an alloy layer, which forms an ohmic contact with the probe body.

5. A microprobe for thermoelectric microscopic measurements, comprising at least one probe body, which has at least one probe tip and a lead electrode, wherein:

the probe body consists of a monocrystalline or polycrystalline semiconductor material and has at least one thermoelectric contact surface;

the semiconductor material is doped or has such a small band gap that intrinsic conductivity occurs at the operating temperature; and the thermoelectric contact surface is exposed at the probe tip or is provided with an alloy layer.

6. The microprobe of claim 5, wherein the semiconductor material is doped in such a way that the resistance of the probe body at room temperature is less than 1,000 ohms.

7. The microprobe of claim 6, wherein the semiconductor material is silicon, germanium, gallium arsenide, III-V semiconductors, or mixed forms of these materials.

8. The microprobe of claim 5, wherein the semiconductor material is silicon, germanium, gallium arsenide, III-V semiconductors, or mixed forms of these materials.

* * * * *